(12) United States Patent
Suri et al.

(10) Patent No.: US 7,217,851 B1
(45) Date of Patent: May 15, 2007

(54) SYNTHESIS OF BUTADIYNES

(75) Inventors: Suresh C. Suri, Lancaster, CA (US);
Michael G. Tinnirello, Palmdale, CA (US)

(73) Assignee: United States of America as represented by the Secretary of the Air Force, Washington, DC (US)

( * ) Notice: Subject to any disclaimer, the term of this patent is extended or adjusted under 35 U.S.C. 154(b) by 472 days.

(21) Appl. No.: 10/817,411

(22) Filed: Mar. 31, 2004

(51) Int. Cl.
*C07C 4/04* (2006.01)
*C07C 2/02* (2006.01)

(52) U.S. Cl. ..................................... 585/534; 585/505

(58) Field of Classification Search ................ 585/534, 585/505
See application file for complete search history.

(56) References Cited

U.S. PATENT DOCUMENTS 3,557,237 A * 1/1971 Pawloski ..................... 585/534
7,083,690 B2 * 8/2006 Dobbins et al. .......... 149/109.6

OTHER PUBLICATIONS

Armin de Meijere, Frank Jaekel, Arndt Simon, Horst Borrmann, Jurgen Kohler, Dan Johnels, and Lawrence T. Scott Regioselective Coupling of Ethynylcyclopropane Units: Hexaspiro[2.0.2.4.2.0.2.4.2.0.2.4]triaconta-7,9,17,19,27,29-hexayne J. Am. Chem. Soc. 1991,113.3935-3941.*

Sergei Kozhushkov, Thomas Haumann, Roland Boese, Burkhardt Knieriem, Stefan Scheib, Peter Bauerle, and Armin de Maeijere The Reactivity of 1,3-Butadiyne Moieties in the 'Exploding' [n] Rotanes- A Crown of Thiophenes Angew. Chem. Int. Ed. Engl. 1995.34.No. 7 p. 781.*

Peter Timmerman, Harry L Anderson, Rudiger Faust, Jean-Francois Nierengarten, Tilo Habicher, Paul Seiler, Francois Diederich Fullerence-Acetylene Hybrids: Towards a Novel Class of Molecular Carbon Allotropes Tetrahedron, vol. 52, No. 14, pp. 4925-4947,1996.*

* cited by examiner

*Primary Examiner*—Thurman K. Page
*Assistant Examiner*—Lalitha Nagubandi
(74) *Attorney, Agent, or Firm*—AFMCLO/JAZ; Thomas C. Stover

(57) ABSTRACT

Provided is a method for the synthesis of 1,4-dicyclopropyl-1,3-butadiyne from CPA. Such butadiyne is prepared by oxidative coupling of cyclopropyl acetylene (CPA) using catalytic amounts each of copper (I)chloride and tetramethylethylenediamine (TMEDA) in isopropanol under aerobic conditions. The resulting butadiyne can serve as a fuel or a fuel additive for combustion in engines propelling motor vehicles, marine vessels, aircraft, rockets and other vehicles.

4 Claims, No Drawings

SYNTHESIS OF BUTADIYNES

RELATED PATENT APPLICATIONS

None

STATEMENT OF GOVERNMENT INTEREST

The invention described herein may be manufactured and used by or for the Government for governmental purposes without the payment of any royalty thereon.

FIELD OF THE INVENTION

This invention relates to synthesis of butadiynes, particularly propyl butadiynes.

BACKGROUND OF THE INVENTION

The compound 1,4-dicyclopropyl-1,3-butadiyne is known in the literature and has been synthesized by oxidative coupling reaction using excessive reagent [CuCl/Cu(OAc)2/Pyridine/MeOH] in moderate yield (56–70%). The reported methods require pyridine as a solvent. The removal and recovery of pyridine are problematic in an industrial scale synthesis and moreover, the reaction requires a long period (e.g., 3 days) of time The synthesis of 1,4-dicyclopropyl-1,3-butadiyne was improved by oxidative coupling reaction of trimethylsilyl cyclopropyl acetylene using CuCl (12 eq.)/Cu(OAc)2 (16 eq.) in MeOH/Pyridine [*Angew. Chem. Int. Ed. Engl.* 1995, ~, 781]. This modification furnished 1,4-dicyclopropyl-1,3-butadiyne in 70% yield in 12 hours.

In addition to the lengthy reaction time and moderate yields, the above processes require the use of pyridine, the recovery and removal of which is problematic.

Accordingly, there is need and market for a process that overcomes the above prior art shortcomings.

There has now been discovered a method for producing the above butadiynes that is of shorter duration, eliminates the use of pyridine and produces the above compound in increased yields over the prior art.

SUMMARY OF THE INVENTION

Broadly, the present invention provides a process for the synthesis of 1,4-dicyclopropyl-1,3-butadiyne in high yields, including adding to cyclopropyl acetylene (CPA), catalytic amounts of CuCl. & tetramethylethylenediamine (TMEDA) in isopropanol, in oxygen atmosphere, to form the above product.

The above process can also be expressed by the following reaction:

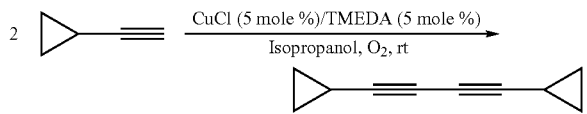

The yield of product by the above inventive method has been up to 90% or more.

The following example serves to illustrate the method of the present invention and should not be construed in limitation thereon.

EXAMPLE I

A clean 1-liter 5-neck flask, equipped with pressure equalizing droping funnel, mechanical agitator, thermometer, sintered sparge tube, and a condenser (chiller set at −5 deg. C), was charged with isopropanol (500 ml), N,N,N',N'-tetramethylethylenediamine (TMEDA) (1.453 g, 0.125 mol) and finely crushed copper (I) chloride (1.237 g, 0.125 mol). An oxygen cylinder was connected via tygon tube to the sintered glass sparge tube. A solution of cyclopropyl acetylene (16.5 g, 0.25 mol) in isopropyl alcohol (125 ml) was taken in a pressure equalizing dropping funnel. The reaction flask was surrounded by a water bath to control the temperature of the reaction mixture. The oxygen was sparged into the vigrously mechanically agitated light green suspension for half an hour. To minimize the evaporation of cyclopropyl acetylene while sparging the reaction mixture with oxygen, the following sequence of operation was repeated until all of the cyclopropyl acetylene was added to the reaction flask.

1. The sparging of oxygen was stopped.

2. A solution of cyclopropyl acetylene (CPA) in isopropyl alcohol (12.5 ml) was added over a period of 10 minutes while maintaining the temperature of the reaction mixture below −30 deg. C.

3. The addition of cyclopropyl acetylene solution was stopped and let the reaction stirred vigrously for 10 minutes.

4. Very slow sparging of oxygen was applied for about 10 minutes.

5. Steps 1–4 were repeated until all of the CPA solution was added to the reaction flask.

The reaction was stirred for three hours. The suspension was filtered over a pad of celite through buchner funnel. The pad of celite was washed with isopropanol (50 ml). The filterate was placed on a rotary evaporator and 80–85% of isopropanol was removed under vacuum. The reaction mixture was cooled in ice/water bath, diluted with and acidified with 1% aqueous hydrochloric acid. The aqueous mixture was extracted with ether (2×50 ml). The organic layer was washed sequentially with saturated aqueous sodium bicarbonate, water and brine. The organic was dried over anhydrous magnesium sulfate. Removal of ether on a rotary evaporator furnished yellow thick liquid that was purified by distillation at 45 deg. C at 0.05 mm of Hg to furnish 14.8 9 of 1,4-dicyclopropyl-1,3-butadiyne in 90% yield.

Thus in the above example, the butadiyne product made by the process of the invention, was synthesized by oxidative coupling of cyclopropyl acetylene (0.25 mol) using catalytic amounts (5 mole %) of cuprous chloride-tetramethylethylenediamine in isopropanol, under aerobic conditions, at room temperature in about a 90% yield.

By "aerobic conditions" as used herein, is meant, in an atmosphere of oxygen.

Accordingly, the present invention has several advantages over prior art methods such as:

1. The use of cupric acetate [$Cu(OAc)_2$] that is used for oxidative coupling reaction of cyclopropyl acetylene using existing literature procedure is totally eliminated.

2. This invention requires only catalytic amounts (5 mole %) each of cuprous chloride [CuCl] and tetramethylethylenediamine [TMEDA].

3. The removal and recovery of pyridine are problematic in an industrial scale synthesis using existing methodologies.

The present invention uses isopropanol as solvent, thus eliminating the use of pyridine.

4. This invention provides very efficient synthesis of 1,4-dicyclopropyl-1,3-butadiyne in greater than 90% yield.

5. This invention also requires less reaction time.

6. This invention is more cost effective as compared to existing procedures for the synthesis of 1,4-dicyclopropyl-1,3-butadiyne.

The present invention uses catalytic amounts of CuCl and TMEDA (about 5 mole % each) in isopropanol under an oxygen atmosphere. The reaction is complete in about two hours and the product, 1,4-dicyclopropyl-1,3-butadiyne, is obtained in about a 90% yield.

Thus, the present invention provides a process for the synthesis of 1,4-dicyclopropyl-1,3-butadiyne. from cyclopropyl acetylene (CPA). The 1,4-dicyclopropyl-1,3-butadiyne is prepared by an oxidative coupling reaction of cyclopropyl acetylene (CPA) using about 5 mole % each of copper (I)chloride-tetrametylethylenediamine (TMEDA) in isopropanol under aerobic conditions.

The inventive butadiyne product is seen as a performance additive in rocket and aircraft fuels and also as a dense fuel in its own right in rocket, missile and aircraft propulsion, including unmanned aircraft.

In other applications, the butadiyne product of the inventive method is seen as an additive to increase density and chemical energy content of propulsion fuel as well to serve as fuel for hypergolic and bipropellant engines.

In addition, such butadiyne product can serve to improve the performance of fuel currently used in combustion engines, such as in motor vehicles, marine craft or other vehicles employing such engines.

What is claimed is:

1. A process for the synthesis of 1,4-dicyclopropyl-1,3-butadiyne in high yields comprising, adding to catalytic amounts of CuCl and tetramethylethylenediamine (TMEDA) in isopropanol, cyclopropyl acetylene (CPA) in isopropanol under aerobic conditions.

2. The method of claim 1 wherein said catalytic amounts are about 5 mole % each, of TMEDA and CuCl.

3. The method of claim 1 wherein said butadiyne is formed by steps comprising:
   a) charging a container with catalytic amounts each of TMEDA and finely crushed CuCl in a solution of isopropanol,
   b.) adding a solution of CPA in isopropanol thereto,
   c.) sparging oxygen into the mixture which then exhibits a green suspension therein,
   d.) siring the solution,
   e) filtering the solution, to obtain a green filtrate and
   f) washing and drying same to obtain high yield 1,4-dicyclopropyl-1,3-butadiyne.

4. The method of claim 3 wherein said catalytic amounts are about 5 mole % each, of TMEDA and CuCl.

* * * * *